United States Patent [19]
Wang et al.

[11] Patent Number: 4,734,378
[45] Date of Patent: Mar. 29, 1988

[54] PRECIPITATION OF INTERFERING PROTEINS IN FLUORESCENCE POLARIZATION IMMUNOASSAY FOR DIGOXIN

[75] Inventors: Philip P. Wang, Libertyville, Ill.; Gloria J. Hockerman, Kenosha, Wis.

[73] Assignee: Abbott Laboratories, North Chicago, Ill.

[21] Appl. No.: 749,344

[22] Filed: Jun. 26, 1985

[51] Int. Cl.$^4$ .................... G01N 1/00; G01N 33/533
[52] U.S. Cl. ................... 436/175; 436/546; 436/817; 436/825
[58] Field of Search ............ 436/537, 539, 800, 815, 436/824, 825, 826, 17, 817, 546; 252/408.1; 435/175

[56] References Cited
U.S. PATENT DOCUMENTS 4,420,568 12/1983 Wang et al. ............... 436/546
4,430,414  2/1984 Swanson ................... 430/152
4,654,311  3/1987 Khanna et al. ............. 436/175
4,698,315 10/1987 Farrenkopf ................ 436/536

OTHER PUBLICATIONS

Agric. Biol. Chem., 43 (7), 1473–1478, 1979, Ohara et al.
Clin. Chem. 30/11, 1826–1829 (1984), Porter et al.
Russian Article, Dissociation Constants of Sulfosalicylic Acid in Mixed Solvents, Porfir'eva et al.

Primary Examiner—David M. Naff
Assistant Examiner—Florina B. Hoffer
Attorney, Agent, or Firm—Alan W. Kowalchyk; Martin L. Katz

[57] ABSTRACT

Interfering proteins are precipitated and digoxin extracted in a fluorescence polarization immunoassay for digoxin with a protein precipitating reagent. The reagent contains about 3 to 4% 5-sulfosalicyclic acid in an aqueous solution including about 40 to 60% of a straight or branch chained organic alcohol having from 1 to 4 carbon atoms.

4 Claims, No Drawings

PRECIPITATION OF INTERFERING PROTEINS IN FLUORESCENCE POLARIZATION IMMUNOASSAY FOR DIGOXIN

BACKGROUND OF THE INVENTION

1. Field of the Invention

This invention relates generally to fluorescence polarization immunoassays and reagents useful therein, and particularly to such an assay for the analyte digoxin in a biological fluid, wherein the assay is improved by the use of a novel precipitation reagent which is effective to extract both the analyte and to precipitate interfering proteins.

2. Background Art

Digoxin is a potent cardiac glycoside widely prescribed for the treatment of patients suffering from congestive heart failure, as well as some types of cardiac arrhythmias. Digoxin intoxication is a common and serious problem in the clinical setting. This is, in part, because cardiac glycosides have a low therapeutic ratio (a very small difference between therapeutic and toxic tissue levels). Coupled with the low therapeutic ratio is a marked patient variability in response to the same dosage of drug, resulting in often unpredictable drug serum levels. Intoxication symptoms are often indistinguishable from the original condition for which the drug was prescribed, and it may not be readily apparent whether the patient has been under- or over-dosed. Monitoring of serum or plasma digoxin levels combined with other clinical data can provide the physician with useful information to aid in adjusting patient dosage, achieving optimal therapeutic effect while avoiding useless subtherapeutic or harmful toxic dosage levels.

Conventional monitoring of digoxin levels in biological fluids such as serum, plasma, urine, spinal and amniotic fluid and the like, has typically depended on commercially available radioimmunoassays (RIA) and nonisotopic assays such as fluorescence polarization immunoassays (FPIA). Certain methodological problems with various commercially-available RIA for digoxin have produced inconsistencies in results from these methods. It has been theorized that variations in the albumin concentration of individual patient serum or plasma samples and in the digoxin standards used, as well as the presence of digoxin-like immunoreactive and/or other presently unidentified substances (especially in patients with renal failure), may account for discrepencies observed between different types of RIA (See W. H. Porter, et al., *Effect of Protein Concentration on the Determination of Digoxin in Serum by Fluorescence Polarization Immunoassay*, Clin. Chem. 30/11, 1826–1829 (1984)).

The use of FPIA for the measurement of therapeutic drugs and other analytes of interest in the foregoing biological fluids is well known in the art. In particular, the advent of FPIA for measurement of human serum and plasma digoxin has enabled significant advantages to be achieved in analysis of this drug over RIA, most importantly in terms of reagent stability, user convenience and speed of analysis. However, investigators have reported that falsely low or high digoxin values may be found with conventional FPIA when the protein concentration of the test sample is abnormally low or high, thus constituting a potential limitation upon such assays when they are used for routine monitoring of digoxin in the laboratory setting (Porter, et al., supra).

One FPIA for serum or plasma digoxin, commercially available from Abbott Laboratories, Abbott Park, Ill. under the registered trademark TDx, utilizes a pretreatment of the sample with substantially an equal volume of 5% trichloroacetic acid solution in water (Abbott Code 9511-30) to precipitate proteins from the sample, thus minimizing interference produced by native background fluorescence of the proteins and improving the signal-to-noise ratio of the assay; e.g., when the assay is carried out using an instrument such as the TDx Fluorescence Polarization Analyzer, also commercially available from Abbott Laboratories. Results of studies of serum digoxin levels measured by this TDx FPIA generally have been favorably compared to those obtained from conventional RIA (Porter, et al., supra). However, these same studies sometimes found that the mean concentrations of digoxin by FPIA generally appeared lower by about 10 to 14 percent, when compared to RIA results. It has been suggested (Porter, et al., supra) that the source of this difference may be that digoxin is bound to the protein precipitate during the pretreatment step, the magnitude of the binding being related to the protein concentration. Therefore, differences between the protein concentration in the calibrators for FPIA (50 grams/liter) and normal serum (60–80 grams/liter) would largely account for low results for digoxin by FPIA. Subsequent research by the present inventors has revealed that approximately 30% of digoxin in typical serum samples is protein-bound. Accordingly, in conventional digoxin FPIA, about 30% of this analyte is coprecipitated, during pretreatment, with the serum proteins, yielding an assay value below that of the actual digoxin present.

SUMMARY OF THE INVENTION

It has now been discovered, and the present invention is based upon this discovery, that FPIA for digoxin such as previously described can be substantially improved by employing the reagent provided by the instant invention. In improved assays according to the invention, direct substitution is made, for conventionally-employed pretreatment solutions, of a novel precipitation reagent which functions to extract the analyte and also to precipitate interfering proteins. Such extraction and precipitation has unexpectedly been found to occur and surprisingly, to occur virtually simultaneously, when in accordance with the invention the reagent which is substituted for the conventional pretreatment solution in the improved FPIA of the invention comprises, in weight/volume percent, from about 3% to about 4% 5-sulfosalicylic acid in an aqueous solution including from about 40% to about 60% of a straight or branch chained organic alcohol having from 1 to 4 carbon atoms.

DETAILED DESCRIPTION OF THE INVENTION

As previously mentioned, the methodology of FPIA for measuring the concentration of drugs or other analytes in biological fluids such as human serum or plasma, is well known. The present invention, although having broad applicability to various FPIA for digoxin in such fluids, and to both manually-performed and semi- or fully-automated assays, is especially advantageous when applied to improve such an assay for digoxin which is commercially available from Abbott Laboratories, Abbott Park, Ill., for use in conjunction with an analytical instrument such as the TDx Analyzer. Accordingly, for purposes of the present disclosure, the invention will be described, in its preferred embodiments, as applied to improve a prior art fluorescence polarization assay for digoxin, which prior art and improved assays can be advantageously performed on a TDx analyzer. A detailed description of reagents and other substances which can be used in an assay which is improved in accordance with the invention (except for the novel reagent of the present invention), and the procedures and techniques for performing the assay, are set forth in detail in U.S. Pat. No. 4,420,568, issued Dec. 13, 1983 and commonly assigned herewith, the disclosure of which patent is hereby incorporated herein by reference.

As previously set forth, the novel precipitation reagent of the present invention comprises a mixture of about from 3% to about 4% (w/v) 5-sulfosalicylic acid, in an aqueous solution of from about 40% to about 60% (v/v) of a straight or branch chained organic alcohol having from 1 to 4 carbon atoms, and the remainder water. The precipitation reagent of the invention is formulated by dissolving the 5-sulfosalicylic acid in a solution of the methanol and water; the reagent then can be used in direct substitution for, e.g., the aforementioned prior art trichloroacetic acid solution in an otherwise well-known assay for digoxin such as has been described. The reagent of the invention has been unexpectedly found to confer upon the assay the advantages mentioned previously.

The following examples describe in greater detail the preparation and use of a preferred embodiment of the reagent of the invention. The specific details of the examples are intended only to illustrate the invention, and are not to be construed as limitative thereof, any limitations being imposed only by the appended claims. For example, it will be appreciated by those skilled in the art that in addition to the preferred use of methanol in the range of quantities as herein described, straight or branched chained alcohols such as ethanol, propanol, isopropanol, and butanol and its isomers, as well as mixtures of these alcohols in various proportions, can be used in quantities within the foregoing range, and the advantages of the invention will also be achieved. Furthermore, while the following examples of assays according to the invention are particularly set forth in terms of assays of human blood serum or plasma, it is apparent that one of ordinary skill in the art, given the teachings hereof, can apply the concepts of the instant invention to the assay of virtually any biological fluid, such as whole blood, urine, spinal and amniotic fluid, and the like.

EXAMPLES

EXAMPLE 1

Preparation of a Preferred Precipitation Reagent

A 30.0 gram quantity of 5-sulfosalicylate was dissolved in a solution of 50% (v/v) methanol and 50% (v/v) water. The final volume was then made up to 1000 ml, maintaining the foregoing percentages of constituents. The reagent so prepared was then used in accordance with the following description in an assay for digoxin on the TDx Analyzer. The use and operation of the TDx analyzer are well known; full details are set forth in the "TDx System Operation" manual, available from Abbott Laboratories, Abbott Part, Ill. The following description relates to the major functional aspects of the TDx Analyzer which are important to the performance of an improved digoxin assay thereon in accordance with the invention, using the precipitation reagent prepared as described in this paragraph.

Reagent/Sample Preparation

Digoxin Calibrators, Controls and a series of human serum samples containing unknown digoxin levels were prepared. A centrifuge tube was designated for each sample to be tested, and placed in a suitable rack. A pipettor was filled with the precipitation reagent prepared as previously described in this example, and 200 microliters of the reagent were dispensed into each centrifuge tube by touching the tip of the pipettor to the wall of the centrifuge tube and depressing the dispensing button on the pipettor. Then, 200 microliters of each serum sample were pipetted into its corresponding centrifuge tube containing the precipitation reagent. After pipetting of the samples, each centrifuge tube was capped and mixed on a vortex mixer for 3-5 seconds, to ensure thorough mixing. The tubes were then placed into a centrifuge head, and centrifuged for about ninety (90) seconds at $9,500 \times g$, until a clear supernatant and a hard compact pellet of denatured protein was obtained. After centrifugation was complete, each tube was uncapped and 250 microliters of the supernatant decanted into the corresponding sample well of a TDx Sample Cartridge (commercially available from Abbott Laboratories), in preparation for performing the digoxin assay. The remainder of the digoxin assay procedure was performed as substantially a routine assay or calibration run would be performed on the TDx Analyzer. In this regard, reference is made to the "Procedures for Operation" section of the "TDx System Operation" manual, previously described, for further details of the protocol used. The following is a description of the major aspects of the performance of the assay.

Assay Operation

All assay steps are controlled by the microprocessor and protocols programmed into the software of the TDx Analyzer. A specific pattern on a barcode label is scanned by a barcode reader and the corresponding protocol is retrieved from the computer memory of the Analyzer. Each protocol contains detailed instructions for movement of pipetting syringes of the Analyzer which determines the volume of sample and reagents used in the pipetting steps, instructions for movement of a boom arm containing an aspirating probe, and for movement of a rotating carousel containing reaction cuvettes, as well as calibrator concentrations used for a calibration curve. The carousel has a unique barcode and set of instructions. Stepper motors, directed by an internal computer, move the carousel, syringes and boom arm. A light beam focused on the carousel and controlled by the microprocessor is used to monitor the number and placement of reaction cuvettes as the carousel rotates past. Two electrodes attached near the end of the probe serve as a liquid level sensor which determines the presence of a liquid by electrical conductivity, thereby minimizing penetration of the probe into the samples and reagents.

The TDx Analyzer automatically pipettes reagents and test samples while simultaneously pipetting dilution buffer, then dispenses both into a reaction cuvette positioned in a rotating carousel. Two pipetting syringes are driven down and the sample or reagent is aspirated at the same time the buffer is being drawn. When both syringes have been filled with the correct volumes, a boom arm moves the probe to the reaction cuvette, and the syringes are driven up, expelling their volumes. The liquids are dispensed at a high velocity creating sufficient turbulence for complete mixing.

Pipetting operations are performed with a dual syringe pump in conjunction with a boom assembly. A 250 microliter syringe is used to aspirate the sample and reagent, and a 2500 microliter syringe dispenses dilution buffer. The syringes are driven by two stepper motors which are computer-controlled for precise pipetting as determined by the assay parameters. The boom assembly consists of an arm which moves vertically and horizontally, teflon tubing which is integral with the teflon probe and liquid level sensor, and a separate barcode reader which moves horizontally with the boom arm. For aspiration of samples or reagents, the boom arm moves in a horizontal arc until the probe is positioned over the proper sample cartridge well. The probe is then moved vertically until the tip comes in contact with the liquid as sample is aspirated. Upon completion of the aspiration, the boom moves up and horizontally, to position the probe over the dilution well or the cuvette. Coordinated rotation of the carousel occurs to bring a sample cartridge or cuvette into the correct position for receipt of the dispensed liquid.

The dilution buffer rests on a platform controlled by a microswitch which signals when the buffer is empty. Teflon tubing connects the buffer bottle to a valve block, liquid heater and boom arm. An integral valve directs the flow of liquids in and out of the syringe and tubing.

Some biological fluids, such as patient blood sera, evidence substantial background fluorescence which must be taken into consideration in order to obtain an accurate measurement of the analyte level in the sample. In the TDx Analyzer, a sample blank for each sample, calibrator or control is automatically made and read before a fluorescent tracer is added to the reaction mixture in each cuvette. To obtain an indication of the true background fluorescence present in the final sample, the mixture on the first reading must be at the final diluted concentration. This is accomplished by adding half the sample volume to a reaction mixture representing half the final reaction mixture. The blank mixtures are measured by the fluorescence detector and the intensities are stored in the computer memory of the instrument.

After the remaining reagents and the rest of the sample are added and incubated, the final reading is made. The blank intensities are subtracted from the final reaction mixture intensities before polarization values are calculated by the TDx Analyzer. The polarization equation becomes as follows:

$$P = \frac{(I_{vv} \text{final} - I_{VV} \text{blank}) - (I_{hv} \text{final} - I_{hv} \text{blank})}{(I_{vv} \text{final} - I_{vv} \text{blank}) + (I_{hv} \text{final} - I_{hv} \text{blank})}$$

The net and blank intensity for each cuvette is also calculated and printed, using the equation $$I_{(Net\ or\ Blk)} = 2I_{hv} + I_{vv}$$

Measuring Fluorescence Polarization

The light source (excitation beam) used for the fluorescence polarization reading on the TDx Analyzer is a tungsten halogen lamp. The light passes through a filter which selects the correct excitation wavelength (usually 485 nanometers), and a reference detector signal is used to monitor the intensity of the lamp. The computer of the instrument can adjust the lamp intensity to provide a constant and accurate measure of the background intensity of samples with naturally fluorescing substances. A liquid crystal-polarizer combination in the light path rapidly polarizes the excitation beam horizontally and then vertically many times in sequence for each reaction cuvette measured. The polarized excitation beam is focused with a lens into the center of the sample, in the reaction cuvette of the carousel. Baffles bordering the cuvette serve as light traps preventing the excitation beam from entering emission optics (polarization detection means) of the instrument. The light path for the emission optics is at a 75 degree angle to the excitation light path. Another lens collimates emitted light and passes it through an emission filter which selects light of a wavelength corresponding, e.g., to the emission peak of fluorescein (525–550 nanometers). Emitted light is then passed through a vertical polarizer, and a photomultiplier tube converts the fluorescence into an electrical current which is recorded as numbers to be entered into the polarization equation by the computerized electronics of the instrument), providing a polarization value for each reaction cuvette measured.

Calculation of Analyte Concentration

The calibration curve for each assay is stored in permanent computer memory of the TDx Analyzer. The stored curve equation is generated by assaying the samples with increasing concentrations of the analyte and measuring the polarization value for each concentration. The appropriate data reduction for that assay calculates a best-fit curve equation using six calibrator concentrations, one of which is zero. Curve parameters of slope, span of polarization value between high and low calibrators, and polarization value of the zero calibrator are used to determine the best fit. Concentrations of the analyte in unknown samples are calculated from this curve equation using the polarization values generated for each sample in the assay.

EXAMPLE 2

Evaluation of Digoxin Precipitation Reagents

The following precipitation reagents were evaulated by using them, as previously described, in an otherwise conventional TDx Digoxin FPIA, following substantially the procedure of Example 1, and utilizing other reagents in the assays which were substantially as described in herein incorporated U.S. Pat. No. 4,420,568. Only reagent I was formulated and used in accordance with the invention; the other reagents were prepared and used for comparative purposes only.

| REAGENT* | | COMPONENTS |
|---|---|---|
| A. | 1% 5-SSA in $H_2O$ | 1 gm of 5-SSA in 100 mL of Water |
| B. | 3% 5-SSA in $H_2O$ | 3 gm of 5-SSA in 100 mL of Water |
| C. | 5% 5-SSA in $H_2O$ | 5 gm of 5-SSA in 100 mL of Water |
| D. | 1% 5-SSA in Methanol | 1 gm of 5-SSA in 100 mL of Methanol |
| E. | 3% 5-SSA in Methanol | 3 gm of 5-SSA in 100 mL of Methanol |
| F. | 5% 5-SSA in Methanol | 5 gm of 5-SSA in 100 mL of Methanol |
| G. | 5% Trichloroacetic Acid $H_2O$ (Prior Art) | 5 gm of Trichloroacetic acid in 100 mL of Water |

-continued

| REAGENT* | COMPONENTS |
|---|---|
| H. 1% 5-SSA in 50% Methanol | Mixture of equal volume of A & D |
| I. 3% 5-SSA in 50% Methanol | Mixture of equal volume of B & E |
| J. 5% 5-SSA in 50% Methanol | Mixture of equal volume of C & F |

*5-SSA = 5-sulfosalicylic acid

The reagents of the foregoing table were tested in the digoxin assay with emphasis on the following criteria:
1. Will the reagent remove all serum protein using the described procedure? (Incomplete removal of serum protein is indicated by a cloudy sample well at the end of the assay protocol).
2. Will the reagent provide a reading in millipolarization units (mP) on the TDx Analyzer of greater than or equal to 90 between the zero and highest calibrator? This is indicated (positively) as span ≧ 90 mP.
3. Will the reagent also extract all the analyte, i.e., digoxin from samples with various protein concentrations? This is indicated (positively) as recovery of ≧ 90% yield.

The test results produced by the foregoing reagants are listed in the following table as "pass/fail", with specific reasons for failure listed as comments. As is apparent from the table, only the reagent which had been prepared according to the invention (Reagent I) produced, unexpectedly, the desired results.

| PRECIPITATION REAGENTS | PASS/FAIL | COMMENTS |
|---|---|---|
| A | Fail | Span <90 mP |
|   |   | Recovery <90% |
| B | Fail | Recovery <90% |
| C | Fail | Recovery <90% |
| D | Fail | Span <90 mP |
|   |   | Recovery <90% |
|   |   | Incomplete serum protein removal. |
| E | Fail | Span <90 mP |
|   |   | Recovery <90% |
|   |   | Incomplete serum protein removal. |
| F | Fail | Span <90 mP |
|   |   | Recovery <90% |
| G | Fail | Recovery <90% |
| H | Fail | Incomplete serum protein removal. |
| I | Pass | According to present invention. |
| J | Fail | Recovery <90% |

EXAMPLE 3

Variation of Alcohol Concentration

To investigate the effect of variation of alcohol concentration in the precipitation reagent of the invention, two solutions of 3% 5-SSA were prepared—one in water and one in methanol. The methanol concentrations investigated were between about 40-60% and they were prepared by mixing the two solutions of 3% 5-SSA with the following formulations:

| 3% 5-SSA in Percentage of Methanol | ml of 3% 5-SSA in Water | ml of 3% 5-SSA in Water |
|---|---|---|
| 40% | 6.0 ml | 4.0 ml |
| 45% | 5.5 ml | 4.5 ml |
| 50% | 5.0 ml | 5.0 ml |
| 55% | 4.5 ml | 5.5 ml |
| 60% | 4.0 ml | 6.0 ml |

All solutions gave an acceptable recovery of >90% (range 9.46%-101.5%).

EXAMPLE 4

Variation of 5-SSA

To investigate the effect of variation of 5-SSA percentage (between 2-5 w/v%) in the precipitation reagent of the invention, the following solutions were prepared and tested for recovery of digoxin from human serum samples with protein concentrations of 9.6 grams per deciliter. Assays were performed substantially as previously described on the TDx Analyzer. Recovery of digoxin was expressed as percent of digoxin recovered by the various precipitation agents relative to digoxin recovered by the 3% 5-SSA aqueous methanol solution.

| % 5-SSA in 50% Aqueous Methanol | Grams of 5-SSA in 100 ml of 50% Aqueous Methanol | % Recovery |
|---|---|---|
| 2.0 | 2.0 | 104 |
|   |   | Incomplete protein removal |
| 2.5 | 2.5 | 111 |
| 3.0 | 3.0 | 100 |
| 3.5 | 3.5 | 99 |
| 4.0 | 4.0 | 96 |
| 5.0 | 5.0 | 82 |

The foregoing results demonstrate that percentages of 5-SSA in precipitation reagents prepared according to the invention which are from about 3% to about 4% (w/v) are effective to provide the aforedescribed advantages; i.e., protein removal and digoxin extraction.

EXAMPLE 5

Comparison to Prior Art Digoxin Assays

Two stock solutions of normal human serum were spiked with digoxin to the same concentration. The stock solutions had protein concentrations of 4.8 and 9.6 grams per deciliter (gm/dL). These solutions were analyzed in an assay according to the invention using precipitation reagent I of Example 1, ("Digoxin II"), a prior art digoxin assay utilizing precipitation reagent G of Example 1 ("Digoxin I"), and the Becton-Dickinson digoxin RIA, Abbott PEG digoxin RIA and DuPont ACA digoxin assay. The results are set forth in the following table.

| [Protein] gm/dL | Digoxin II | Digoxin I | [Digoxin] nanograms/ml Becton-Dickinson | Abbott PEG | DuPont ACA |
|---|---|---|---|---|---|
| 9.6 | 1.41 | 0.88 | 1.39 | 1.81 | 1.32 |
| 4.8 | 1.44 | 1.32 | 1.33 | 1.42 | 1.48 |

The foregoing results demonstrate surprisingly good correlation between measurement of digoxin levels using assays employing the novel precipitation reagents of the invention with RIA of the prior art and the DuPont assay, demonstrating the greatly improved results obtainable by use of the novel precipitation reagent of the invention over prior art FPIA.

EXAMPLE 6

Effect of Elevated Protein in Plasma Samples

Further experiments were carried out to show the advantages of use of the precipitation reagent of the present invention to precipitate protein and extract digoxin in human plasma samples, by comparison with the use of a prior art TCA extractant. The results of FPIA conducted as previously described are set forth in the following table.

| Trichloroacetic Acid (TCA) | | BSA** | Globulin** | 99800 |
|---|---|---|---|---|
| Extraction (Prior Art) | | | | |
| Digoxin | Low Control | 0.39 | 0.37 | 0.52 |
| Level | Med Control | 0.91 | 1.04 | 1.49 |
| (nanograms/ml) | High Control | 2.56 | 2.93 | 3.49 |
| 3% 5-SSA 50% MeOH Extraction (Present Invention) | | | | |
| Digoxin | Low Control | 0.63 | 0.60 | 0.66 |
| Level | Med Control | 1.31 | 1.33 | 1.49 |
| (nanograms/ml) | High Control | 3.40 | 3.84 | 3.65 |

**99800 Plasma (protein about 6.0 gm %) spiked with specific protein to give 10.0 gm %

The foregoing results demonstrate an unexpected, greatly enhanced ability of FPIA utilizing the precipitation reagent provided by the invention to obtain improved measurement of digoxin in plasma as well as serum, by comparison with the use of TCA pretreatment in such assays of the prior art. Thus, it is apparent that the invention enables substantially more accurate results to be achieved for high-protein samples.

It is apparent that numerous modifications and variations can be made in the specific formulations and preocedures described herein for preferred embodiments of the invention, without departing from the spirit and scope of the invention, as defined solely by the following claims.

What is claimed is:

1. In a method for pretreating a test sample of biological fluid prior to a fluorescence polarization immunoassay for digoxin of said test sample wherein a precipitation reagent is employed to remove interfering proteins from the sample, the improvement comprising: intermixing said sample with a precipitation reagent comprising, in weight/volume percent, from about 3% to about 4% 5-sulfosalicylic acid in an aqueous solution having from about 40% to about 60% of a straight or branch chained organic alcohol having from 1 to 4 carbon atoms.

2. The improvement of claim 1, wherein the organic alcohol is present in an amount of about 50% (volume/volume) of the aqueous solution.

3. The improvement of claim 1, wherein the organic alcohol is methanol.

4. The improvement of claim 1, wherein the organic alcohol is selected from the group consisting of methanol, ethanol, propanol, butanol and mixtures thereof.

* * * * *